(12) United States Patent
Veillet et al.

(10) Patent No.: US 8,236,359 B2
(45) Date of Patent: Aug. 7, 2012

(54) USE OF PHYTOECDYSONES IN THE PREPARATION OF A COMPOSITION FOR ACTING ON THE METABOLIC SYNDROME

(75) Inventors: Stanislas Veillet, Savigny sur Orge (FR); Rene Lafont, Paris (FR)

(73) Assignees: Institut Biophytis SAS, Paris (FR); Universite Pierre et Marie Curie, Paris (FR); Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 12/745,315

(22) PCT Filed: Nov. 19, 2008

(86) PCT No.: PCT/FR2008/052088
§ 371 (c)(1),
(2), (4) Date: Oct. 28, 2010

(87) PCT Pub. No.: WO2009/071804
PCT Pub. Date: Jun. 11, 2009

(65) Prior Publication Data
US 2011/0033561 A1    Feb. 10, 2011

(30) Foreign Application Priority Data

Nov. 30, 2007 (FR) .................................. 07 59478

(51) Int. Cl.
*A61K 36/00* (2006.01)
(52) U.S. Cl. ........................................ 424/725; 514/909
(58) Field of Classification Search ........................ None
See application file for complete search history.

(56) References Cited

FOREIGN PATENT DOCUMENTS

| CN | 1557324 | | 12/2004 |
|---|---|---|---|
| CN | 101011436 A | * | 8/2007 |
| GB | 2 420 066 | | 5/2006 |
| JP | 63002928 A | * | 1/1988 |
| JP | 4-124135 | | 4/1992 |

OTHER PUBLICATIONS

Monday et al, Effects of the ingestion of *Serratula tinctoria* extracts, a plant containing phytoecdysteroids, on the development of the vineyard pest *Lobesia botrana* (Lepidoptera: Tortricidae), Archives of insect biochemistry and physiology, 1997. vol. 35, No. 1/2. p. 227-235.*
Tarui et al, Visceral fat obesity: anthropological and pathophysiological aspects, International journal of obesity, (Sep. 1991) vol. 15 Suppl 2, pp. 1-8.*
Zainullin et al, Biological efficiency of two fodder additives contained ecdysteroids of *Serratula coronata* L., Rastitel'nye Resursy (2003) vol. 39, No. 2, pp. 95-103.*
Wyatt et al, Overweight and obesity: prevalence, consequences, and causes of a growing public health problem, The American journal of the medical sciences, (Apr. 2006) vol. 331, No. 4, pp. 166-174.*
Wilding, Causes of obesity, Practical Diabetes International, (2001) vol. 18, No. 8, pp. 288-291.*
Hansen et al, Causes of obesity and consequences of obesity prevention in non-human primates and other animal models, International textbook of obesity, (2001) pp. 181-201.*
Metabolic syndrome from Merck manual, accessed on Jun. 12, 2011, pp. 1-2.*
Simpson et al., The prevention of type 2 diabetes-lifestyle change or pharmacotherapy? A challenge for the 21st century. Diabetes Research and Clinical Practice 59 (2003) 165-180.*
Ernsberger et al, Metabolic effects of antihypertensive agents: role of sympathoadrenal and renin-angiotensin systems, Naunyn-Schmiedeberg's Archives of Pharmacology (2006), 373(4), 245-258.*
Database WPI Week 1992 Thomson Scientific, London, GB; AN 1992-189214, XP002483882 "New steroidal insect metamorphosis hormone, e.g. alpha-ecdysone, inokosterone and pterosterone, for treating diabetes".
Database WPI Thomson Scientific, London, GB; AN 2005-243149, XP002483883, "Use of ecdysteronein preparation of insulin resistance medicine".
Dtatabase TCM-SIPO, SIPO; CN1280010, Kunming Pharmaceutical Co. Ltd., Oct. 17, 2001, Yang.: An oral medicine for the treatment of diabetes and its preparation method, XP002483879.
Zhu N. et al., "Ecdysteroids of quiona seeds (*Chenopodium quiona* Willd)", J. Agric Food Chem., vol. 49, 2001, pp. 2576-2578, XP002483876.
Kutepova T.A. et al., "Hypoglycemic activity of the total ecdysteroid extract from *Ajuga turkestanica*", Pharm. Chem. J., vol. 35, No. 11 2001, pp. 608-609, XP002483877.
Database CA Chemical Abstracts Service, Columbus Ohio, US; Doklady Akad. Nauk Respub. Uzbekistan (4) 46-49, 1997, Syrov V. N. et al., "Hypoglycemic action of phytoecdysteroids and some mechanisms of its realisation in experimental animals", XP002483880.
Database Biosis Biosciences Information Service, Philadelphia, PA US; Voprosy Meditsinskoi Khimii, vol. 28, pp. 101-105, 1982, Mironova V. N. et al., Hypocholesterolemic action of phytoecdysones in experimental hypercholesterolemia in rats, XP002483881.
Lafont R. et al., "Practical use of ecdysteroids in mammals including humans: an update", J. Insect Sci., vol. 3, No. 7, 2003, pp. 1-30, XP002483878.

(Continued)

*Primary Examiner* — Qiuwen Mi
(74) *Attorney, Agent, or Firm* — Young & Thompson

(57) ABSTRACT

For reducing the negative effects of the metabolic syndrome on mammal organisms, it is proposed to use phytoecdysones for diminishing the fat body mass in individuals, notably with a weight excess. Phytoecdysones are advantageously incorporated into a food composition. The phytoecdysones can come from food plants, such as quinoa.

6 Claims, 3 Drawing Sheets

OTHER PUBLICATIONS

Catalan R. E. et al., "Alterations in rat lipid metabolism following ecdysterone treatment", Comparative Biochemistry and Physiology. B. ComparativeBiochemistry, Pergamon Press, London, GB, vol. 8, No. 3, Jan. 1, 1985, pp. 771-775, XP023529585, ISSN: 0305-0491.

International Search Report dated Mar. 9, 2010, from corresponding PCT application.

* cited by examiner

USE OF PHYTOECDYSONES IN THE PREPARATION OF A COMPOSITION FOR ACTING ON THE METABOLIC SYNDROME

TECHNICAL FIELD

The invention relates to the use of phytoecdysones, in a pure form or in the form of an extract, in the preparation of a composition for preventing or treating the metabolic syndrome in mammals. More particularly the use according to the invention enables to reduce the fat body mass and/or to reduce its accumulation notably in the abdominal region. The invention also relates to a plant extract enriched with phytoecdysones which can be used in the preparation of such a composition. The invention can be advantageously used in the food-processing industry for enriching food products with phytoecdysones in order to obtain functional foods, or medicinal foods. The invention also finds application in the medical field, phytoecdysones being used for example in a medicinal composition.

STATE OF THE ART

Nowadays, weight excess is a widespread physiological condition, whatever the age group and the culture. This physiological disorder can be at the root of a lot of health complications. For example, the metabolic syndrome is a physiological disorder which is mostly linked in an individual to a weight excess. It is admitted that a person suffers from the metabolic syndrome when he/she shows at least three of the five clinic signs linked to this condition, namely a visceral or abdominal obesity, a hypertriglyceridaemia, a atherogenic dyslipaemia, an hypertension or hyperglycaemia (Isomaa et al., 2001). Moreover, obesity increases in itself the risks of developing a type II diabetes, or fat diabetes, and cardiovascular diseases (Rexrode et al., 1998).

A lot of drugs, such as hypotensive and hypocholesterolaemic drugs have been developed for preventing cardiovascular diseases from developing in high-risk individuals (Foster-Schubert et al., 2006). Insulin can also be administered to diabetic persons when the prescription of a diet low in fat and sugar is not sufficient anymore.

However, for the majority of individuals suffering from the metabolic syndrome, the administration of a drug mixture associated to the prescription of a strict diet and to the necessity of practicing a regular physical exercise, is rather discouraging, all the more as the beneficial effects are not immediate and as the efforts for a healthier life must be maintained, otherwise there is a risk to see the recurrence of the symptoms associated to the metabolic syndrome (Wasan et al., 2005).

It is thus necessary that individuals suffering from the metabolic syndrome can recover a physiologic balance so that they are not considered anymore as high-risk individuals, notably as regards the development of cardiovascular diseases, without having to bear too heavy and/or too demanding a treatment. It is also necessary to avoid the installation of all or part of the associated symptoms, which can lead to the loss of lean body mass and to the diagnosis of the metabolic syndrome (Unger, 2003).

A balanced diet supplemented with functional foods or dietary supplements enables to act on the health condition of mammals with a weight excess and to prevent the installation of the metabolic syndrome. A lot of dietary supplements or functional foods have been developed for favoring the weight loss in mammals with a weight excess (Saper et al., 2004) and for preventing the development of diabetes (McWorther, 2001) and of cardiovascular diseases. The majority of the food products, currently on the market, show an insufficient effectiveness for treating the abdominal obesity and, in some cases, they proved to be toxic (Pittle et al., 2005). It is thus necessary to identify new natural molecules, already present in diet for mammals, in order to develop ingredients and functional foods that are non toxic and effective on the fat body mass.

Phytoecdysones are natural molecules which belong to the triterpene family and which are present in a relatively large quantity in the plant kingdom where they can be found in 5% of the wild plants (Báthori et Pongrács, 2005). The physiologic effects of phytoecdysones, notably of the 20-hydroxyecdysone, in mammals have been studied by several teams. Notably, it has been shown that these molecules stimulate the protein syntheses (Otaka et al., 1968; Khimiko et al., 2000; Syrov, 2000) and the growth in animals (Purser and Baker, 1994). Hypoglycaemic effects (Uchiyama et al., 1970; Mironova et Kholodova, 1982; Takahashi et Nishimoti, 1992; Yang et al., 2001; Chen et al., 2004, 2006), hypolipidaemic effects (Mironova et al., 1982 Syrov et al., 1983) and cholagogue effects (Syrov et al., 1986) have also been reported. Besides, theses molecules show antioxidant properties (Kuzmenko et al., 2001) and are toxicity-free.

DESCRIPTION OF THE INVENTION

The inventor have found that the ingestion, regular or not, of phytoecdysones enables to positively act at least on the accumulation of fat body mass, essentially in the abdominal region. Phytoecdysones are ecdysones from plants. "To positively act" means that the ingestion of phytoecdysones enables to reduce the fat body mass in already obese mammals, even though the diet should favor the increase of fat body mass, whether the mammal is growing or is in adulthood. The ingestion of phytoecdysones enables to diminish the fat body mass, but also acts on hyperglycaemia and atherogenic dyslipaemia, and therefore enables to prevent or treat the metabolic syndrome in obese individuals or individuals with a weight excess.

An individual is considered as having a weight excess when his/her Body Mass Index (BMI) is higher than 25, and is considered as obese when the BMI is superior or equal to 30.

The invention proposes thus to supply phytoecdysones in a composition for mammals, or in a medicinal composition, in order to suppress or prevent the apparition of the metabolic syndrome. The diminution of the already acquired fat body mass can enable some individuals not to suffer anymore from the metabolic syndrome. Indeed, the diminution of the fat body mass has an indirect effect on several symptoms associated to the metabolic syndrome, and notably on the abdominal obesity, on glycaemia and atherogenic dyslipaemia. Moreover, it can also have a preventive action on the development of the metabolic syndrome in persons with a weight excess, by enabling a diminution of the already acquired fat body mass and/or by preventing them to put on supplemental weight.

More generally, the use of phytoecdysones according to the invention enables to prevent the accumulation of the abdominal fat body mass and to diminish the already acquired abdominal fat body mass in individuals, whatever his/her BMI, and it enables to prevent and/or treat the metabolic syndrome in obese individuals or individuals with a weight excess.

Phytoecdysones can be supplied in a pure form or in the form of a more or less enriched plant extract. Advantageously, the plant extract enriched with phytoecdysones according to the invention comes from a quinoa extract. Indeed, quinoa is a comestible pseudo-cereal which is naturally rich in phytoecdysones (Zhu et al., 2001; Dini et al., 2005). It is thus possible to supplement the diet with the ingestion of quinoa extract enriched with phytoecdysones, by introducing this extract into a food, such as a milk product or a drink, or by consuming it as a dietary supplement, for example in the form of capsules. Quinoa is particularly interesting in that it is a plant of the human diet, such as wheat or buckwheat, but not a medicinal plant some side effects of which could be ignored. The inventors took a particular interest in quinoa not only for its nutritional qualities but also because it naturally possesses an important amount of phytoecdysones.

The ability to produce phytoecdysones seems to be lost for the great majority of the cultivated plant species, and therefore the "conventional" human diet contains only small quantities of phytoecdysones, that is in average less than 1 mg per day. Quinoa represents to date the food plant which is far and away the richest in phytoecdysones (Zhu et al., 2001). These phytoecdysones are present in large quantities in the covering membranes of quinoa seeds. For example, an intake of 60 grams of quinoa seeds (dry weight) comprises between 15 and 20 milligrams of 20-hydroxyectydone.

Spinach and some mushrooms can also be advantageously used for producing a plant extract rich in phytoecdysones (Findeisen E., 2004).

The purpose of the invention is a use of phytoecdysones, pure or contained in a plant extract particularly enriched with phytoecdysones, in the production of a composition for diminishing the abdominal fat body mass in mammals. Notably, it enables to diminish the already acquired abdominal fat body mass. It also enables, notably in the case of a hyperlipidical diet, to diminish the accumulation of abdominal fat body mass.

According to the invention, the composition comprising phytoecdysones is particularly intended to individuals with a weight excess or to obese individuals, and enables to prevent and/or to treat the metabolic syndrome.

The so-prepared composition can be consumed by a person with a weight excess and suffering from a metabolic syndrome or likely to develop a metabolic syndrome. The regular intake of the composition according to the invention helps diminish the fat body mass, notably in the abdominal region. The risks of complications diminish as the fat weight excess diminishes.

The composition means for example a food product such as a drink, a milk product or other. Of course, the composition can be a medicinal composition used for example in the form of pills containing thus a highly precise dose of phytoecdysones. "medicinal composition" means a composition that has curative and/or preventive properties against the accumulation of fat body mass or indirectly against the metabolic syndrome and the intake of which is subjected to an more or less strict aftercare. The consumption in the form of pills is advantageous in that the consumer is able to evaluate in a sure manner the amount of phytoecdysones consumed, and regardless his/her appetite. Of course, the association of phytoecdysones with a food, i.e. the consumption of phytoecdysones in the form of a food composition, enables to go beyond the notion of treatment and consequently of constraints linked to a specific clinical condition.

The phytoecdysones used can be obtained by extraction, from plants containing phytoecdysones. The phytoecdysones used can also be synthetic phytoecdysones. In the case of an extraction, the plant extract used is preferably an extract of food plants such as quinoa. "Food plants" mean plants that are essentially used as food or as condiment in a large geographical zone. On the other hand, medicinal plants are plants that are essentially used for their curative power.

The purpose of the invention is also an extract of food plants enriched with phytoecdysones. Advantageously, said extract comprises at least 1% and preferably between 1% and 7%, in a preferred manner between 1.5% and 3% and more preferably 2%, in weight of phytoecdysones.

Plants from which the extracts according to the invention are obtained are advantageously selected from quinoa, spinach and mushrooms.

The purpose of the invention is also a food composition for mammals, comprising a plant extract enriched with phytoecdysones.

DETAILED DESCRIPTION

Figure 1:
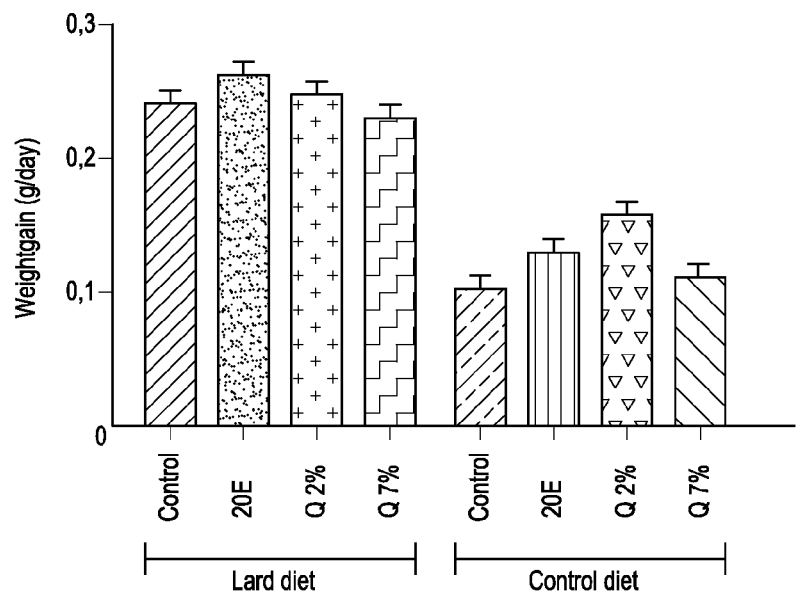
FIG. 1 shows a graph representing the weight gain in g/day according to the diet to which the mice are subjected.

According to the invention, it is proposed to supply a concentrated dose of pure phytoecdysones, or through a plant extract enriched with phytoecdysones, in order to improve the sanitary condition of persons with a weight excess, or to avoid a weight excess due to the accumulation of abdominal and visceral fat body mass. It is one of the basic clinic markers of the metabolic syndrome and a risk factor for developing cardiovascular diseases and type 2 diabetes.

The threshold dose of phytoecdysones contained in a composition according to the invention and enabling to obtain positive effects on the fat body mass is from 0.3 to 0.5 mg/kg in humans, i.e. from 20 to 30 mg per day on average. This estimation is based on the detection of a physiological effect in mice (Mus musculus line C57BI6) at a dose of 5 mg/kg. This dose has been adjusted with a pharmacological correspondence factor taking into account an average half-life of phytoecdysones which is higher in humans than in mice (Simon and Koolman, 1989).

According to the invention, it is possible to supply this daily dose of phytoecdysones in the form of a plant extract, such as quinoa, incorporated for example into a food commonly used by an individual. Indeed, in 4 grams of quinoa extract enriched with 0.5% in weight of phytoecdysones, there are 20 milligrams of phytoecdysones. To obtain the same quantity of phytoecdysones from quinoa seeds, from 50 to 100 grams of untreated quinoa seeds should be consumed (Dini et al., 2005). The quinoa extract according to the invention can thus contain up to 50 times as many phytoecdysones than the quinoa seeds from which the extract is obtained. It is thus quite conceivable, with the use according to the invention, to cover the phytoecdysone needs of individuals, without any food constraints, since the desired dose can be supplied by ingesting only one common food, such as a yoghurt. The extract according to the invention can be added at the time of elaboration of a food composition, in order that the finished food contains it. Thus, some foods or drinks, sold in supermarkets or hypermarkets, will contain a given dose of phytoecdysones. It is also possible to add the extract enriched with phytoecdysones to cereals when they are consumed, before or after cooking them. In that case, the individual can adapt the quantity of phytoecdysones to his/her own needs.

According to an example of the invention, the plant extract enriched with phytoecdysones is introduced into everyday foods, i.e. foods that are above all consumed for a nutritive, but not therapeutic or prophylactic reason.

From a quantitative point of view, every individual can consume several hundred kilograms of a same food per year. When a plant extract enriched with phytoecdysones is added to this type of basic consumer foods, the consumers can receive a sufficient dose of phytoecdysones for preventing the apparition of a weight excess due to too important an accumulation of fat notably in the abdominal region, or the aggravation of their conditions, without needing a treatment. This enriched extract can be considered as an "adaptogenic" substance (Báthori et Pongrács, 2005). "Adaptogenic substance" means a substance which is not a medicament but which improves the general balance for making the individual more resistant and for preventing him/her from developing diseases associated to the metabolic syndrome in case of a weight excess.

Quinoa is advantageous in that it is a plant easy to grow, with no particular care, with few water needs and withstanding utmost severe growing conditions.

In addition, phytoecdysones obtained from quinoa are not thermolabile. It is thus possible to prepare food compositions intended to be heated or cooked with a quinoa extract enriched according to the invention.

Of course, according to another example of the invention, the same quantities of phytoecdysones can be supplied to a patient by ingestion of a medicinal composition comprising the prescribed dose of phytoecdysones, the composition being delivered for example in the form of capsules or tablets.

I] Examples of a Method for Preparing a Quinoa Extract Enriched with Phytoecdysones

EXAMPLE 1

Method A

A sequential extraction with water is carried out by adding 500 g of quinoa seeds to 2 l of boiling water, and the mixture is maintained for 5 minutes at 80° C. The water is eliminated and a second extraction is carried out with 2 l of a mixture ethanol-water (1:1) while stirring for 20 minutes at 80° C.

Such a sequential extraction enables to suppress from the extract saponins contained in large amounts in quinoa seeds (Muir et al., 2002), which would otherwise add a bitter flavor to said extract.

The ethanolic extract is filtered on Miracloth™, evaporated to dryness and added with 400 ml of absolute ethanol, which gives a large amount of insoluble residue.

The ethanolic fraction is filtered or centrifuged and then dried.

The chromatographic analysis (HPLC) shows that this extract contains 2±0.2% in weight of 20-hydroxyecdysone.

EXAMPLE 2

Method B 50 g of quinoa seeds are mixed to 400 ml of distilled water. The mixture is introduced into a microwave oven for 5 minutes at an average power (800 W).

Then, a second extraction is carried out with ethanol (400 ml of ethanol) for 2.5 min in the microwave oven, still at an average power (800 W).

Both extraction methods enable to obtain between 150 and 200 milligrams of phytoecdysones per kilogram of treated quinoa seeds, of which 85-90% correspond to the 20-hydroxyecdysone, and the remainder to ecdysteroids with a very similar structure.

EXAMPLE 3

Method C for Enriching the Extract

It is possible to enrich the extract of the method A (or B) by means of a partition butanol-water, which enables to eliminate the most polar compounds and, after evaporation of the butanol phase, to obtain an extract more concentrated in phytoecdysones (5-7% in weight).

II] Experimental Study of the Effect of Phytoecdysones on the Storage of Fat Body Mass.

Protocol

A test is carried out for studying the effect of phytoecdysones on mice subjected to a fat diet for three weeks The fat diet or inductor diet consists in supplying large amounts of fat matter in the form of lard. The mice selected for this study are male mice C57 BL/6, 6-weeks old at the beginning of this inductor diet. Such mice are a preferred study model for analyzing the impact of the quinoa extract enriched with phytoecdysones according to the invention on the physiological parameters of the metabolic syndrome.

At the same time, another test is carried out for studying the effect of these same phytoecdysones on mice which have not been subjected to a fat diet, which is considered as a normal control diet.

The table 1 below indicates the distribution of the studied mice according to diets and treatments to which they have been subjected.

TABLE 1

Distribution of the studied mice

| | | | Treatments | | |
| --- | --- | --- | --- | --- | --- |
| | | Control | Pure Active ingredient 20E | Extract 1.6% | Extract 7% |
| Diets | Inductor | 6 mice | 6 mice | 6 mice | 6 mice |
| | Control | 6 mice | 6 mice | 6 mice | 6 mice |

The inductor diet is a diet enriched with lard.

The pure active ingredient is pure 20-hydroxyecdysone (20E).

The 24 mice of each series have been subjected to a diet, such as detailed in the table 2, for three weeks and have been treated at the same time with the pure molecule, or a quinoa extract enriched up to 1.6% (2.24% the last treatment week for the control series) or 7% of 20-hydroxyecdysone (20E). The concentration of 20-hydroxyecdysone is adjusted to 40 mg per kg of food.

While taking account of the amount of food ingested on average by the mice, the administered dose of 20E corresponds in the three treatments to 5 mg of 20E per kg of the body weight and per day. The food is supplied in excess, three times a week, for both diets and the three treatments. On average, 40 g of food are supplied for each cage and per day, i.e. 6.5 g of food for each mouse and per day.

The table 2 below indicates in more detail the composition of the food diet to which the mice are subjected.

TABLE 2

Diet composition

| Ingredients | Composition (g/kg) | |
| --- | --- | --- |
| | P14 Control | P14 Lard |
| Milk (LR85 F) | 140 | 170 |
| Starch | 622.4 | 360 |
| Saccharose | 100.3 | 57 |
| Soy oil | 40 | 40 |
| Lard | 0 | 235 |
| Mineral salts | 35 | 62.5 |
| Vitamins | 10 | 1.5 |
| Cellulose | 50 | 62.5 |
| Choline | 2.3 | 2.3 |

Sacrifice:

At the time of the sacrifice, the weight of the mice (Bwt), as well as the weight of the liver, the epididymis adipose tissue (EAT) and the subcutaneous adipose tissue (SCAT) are measured.

Cells of the epididymis adipose tissue are taken for carrying out a count and a morphological analysis.

Results

Weight Gain

In FIG. 1, it is represented a graph showing the weight gain in g/days for the mice according to their diet and the associated treatment.

As expected, it is noted that the mice subjected to a lard diet have a higher weight gain than those without any lard supply. The mice subjected to the lard diet have gained on average 250 mg/day, and whatever the treatment. On the other hand, the treatment, whatever it be, does not significantly modify the weight gain for the group of mice supplied with lard as well as for the group of mice subjected to a control diet.

Measure of the Fat Body Mass

Figure 2:
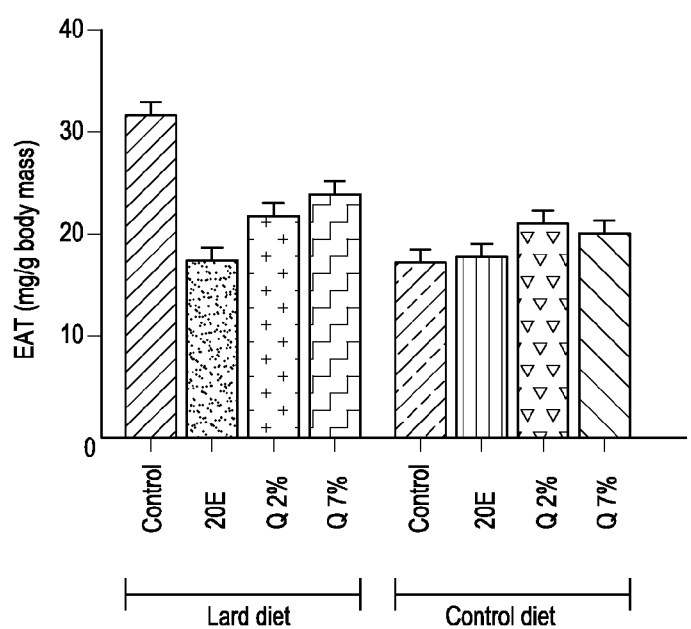
FIG. 2 shows a graph representing the percentage of epididymis adipocytes (% EAT in mg/g BW) according to the diet to which the mice are subjected.

In FIG. 2 it is represented a graph showing the amount of fat body mass in the gonad tissue (% EAT) according to the diet and the associated treatment.

As expected, it is noted a higher increase in adiposity in control mice subjected to the lard diet than in control mice subjected to a normal diet. In mice subjected to a treatment, in association with the lard diet, the treatment with the pure molecule and the 2% and 7% extracts results in a decrease of the adiposity of 50%, 30% and 20%.

The mice subjected to a treatment with 2% and 7% extracts in association with the control diet shows an adiposity which is slightly higher than that of the untreated mice, but this effect is not significant. On the other hand, the treatment with the pure molecule does not modify the adiposity of the mice subjected to the control diet.

Figure 3:
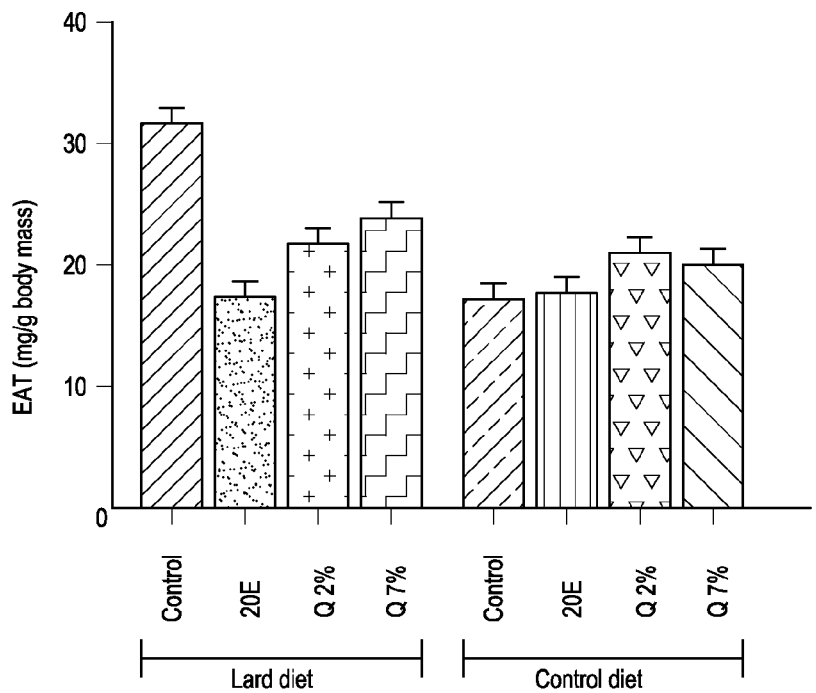
FIG. 3 shows a graph representing the subcutaneous adiposity (% SCAT in mg/g BWT) according to the diet to which the mice are subjected.

In FIG. 3 it is represented a graph showing the amount of fat body mass in the subcutaneous inguinal tissue according to the diet and the associated treatment.

The results are similar to those concerning the adiposity in the gonad tissue. In mice subjected to the lard diet, the decrease is however less important with the treatment with 2% and 7% extracts. In mice subjected to the control diet, there is no significant effect of the treatments.

Measure of Adipocytes

The adipose cells, or adipocytes, are cells constituting adipose tissue. These cells comprise in their cytoplasm a lipid droplet playing an essential role in the synthesis of lipids and their storage. It is conceivable that a diminution of the diameters of these cells, because of the diminution of the diameter of the lipid droplet, will have an effect on the amount of the stored fat body mass.

Figure 4:
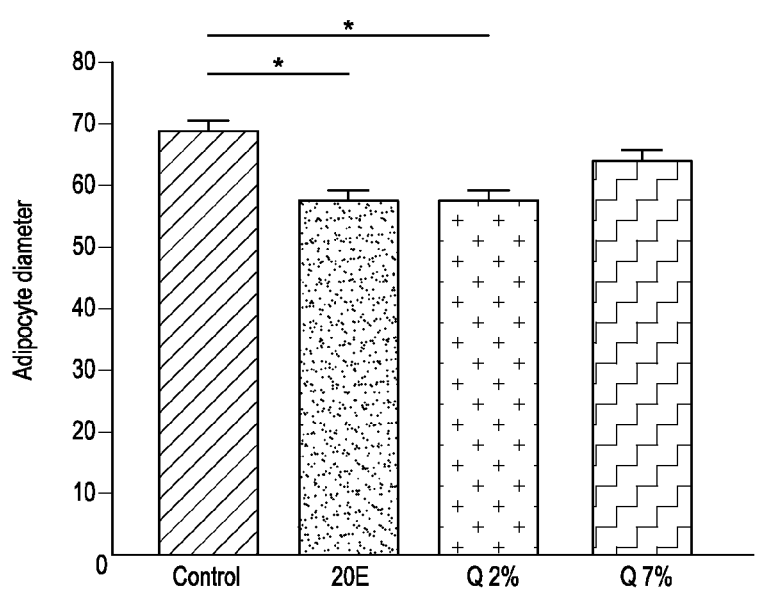
FIG. 4 shows a graphic representing the adipocyte diameter, in μm, according to the treatment administered to the mice subjected to the lard diet.

In FIG. 4, it is represented the effect of the treatment on the diameters of the adipocytes. In mice subjected to the lard diet, the adipocytes are hypertrophied in diameter in comparison with those of the control mice. The treatment with the pure molecule and with the 2% extract reduces the adipocyte sizes in a significant manner. On the other hand, the 7% extract has no significant effect on the adipocyte diameters.

Figure 5:
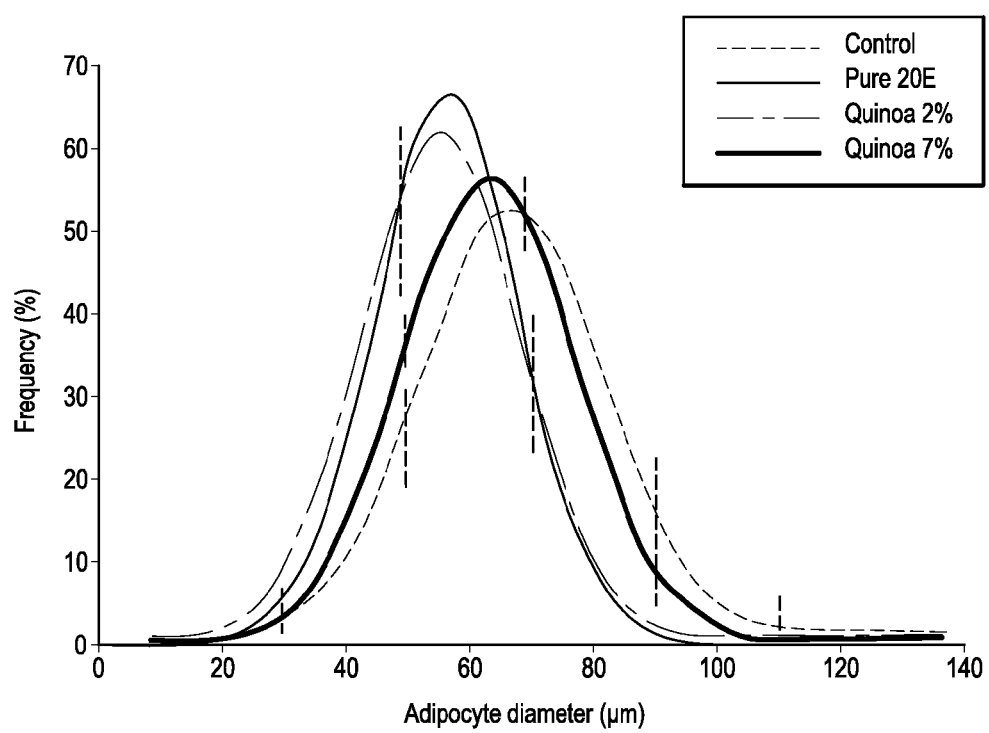
FIG. 5 shows a graph representing the distribution of the adipocyte diameters according to the treatment administered to the mice subjected to the lard diet.

In FIG. 5, it is represented the effects of the treatment on the distribution of the adipocyte diameters.

The control mice subjected to the lard diet show a distribution with a majority of cells with an important diameter (up to 110 nm with a mode of about 70). The mice to which pure phytoecdysone has been administered show a distribution with a maximum diameter of 90 nm, with a mode of 60. The mice to which the 2% extract has been administered show a similar distribution with a majority of small-sized cells. The mice to which the 7% extract has been administered show a distribution between that for lard diet and that for the 2% extract.

CONCLUSION

The administration of the pure molecule, as well as that of the 2% extract, avoid a development of the an obesity induced by a hyperlipidical and hypercalorific diet and has no effect in non obese animals with a normal diet, i.e. a diet which is neither hypercalorific nor hypocalorific. This effect is similar on the gonad tissue and on the subcutaneous tissue. The 7% extract induces a small (subcutaneous) adiposity in the case of the control diet and shows a diminution of the adiposity equivalent to that for the 2% extract in the case of the lard diet.

The comparison of the results of the adiposity with that of the weight gain shows that the mice grow and put on weight without having any fat body mass. There is probably an increase of lean body mass in muscles.

III] Example of Formulation of 2% Quinoa Extract in a Galenical Form Such as Capsules 375 mg of quinoa extract enriched with phytoecdysones up to 2% in weight are added to 75 mg of manioc flour. The mixture is introduced into a 360 mg-type capsule. With one capsule a patient absorbs 7.5 mg of phytoecdysones. The recommended dosage, in the case of a weight excess that can be diagnosed as a risk for a patient from the medical complication point of view and notably for the installation of the metabolic syndrome, is four capsules per day, so that the patient receives daily 30 mg of phytoecdysones.

REFERENCES

Báthori M, Pongrácz Z 2005 Phytoecdysteroids—from isolation to their effects on humans. *Curr. Med. Chem.* 12 153-172.

Chen Q, Xia Y, Qiu Z 2004 Use of ecdysterone in preparation of insulin resistance formulation. Application CN 1002-1686 20040113 (*Chemical Abstracts* 143 159564).

Chen Q, Xia Y, Qiu Z 2006 Effect of ecdysterone on glucose metabolism in vitro. *Life Sci.* 78 1108-1113.

Dini I, Tenore G C, Dini A 2005 Nutritional and antinutritional composition of Kancolla seeds: an interesting and underexploited andine food plant. *Food Chem.* 92 125-132.

Findeisen E 2004 Ecdysteroide in der menschlichen Nahrung. Ph.D. Thesis, University of Marburg (Germany).

Foster-Schubert K E, Cummings D E 2006 Emerging therapeutic strategies for obesity. *Endocrine Rev.* 27, 779-793.

Isomaa B, Almgren P, Tuomi T, Forsén B, Lahti K, Nissén M, Taskinen M R, Groop L 2001 Cardiovascular morbidity and mortality associated with the metabolic syndrome. *Diabetes Care* 24, 683-689.

Khimiko I N, Mitrokin Yul, Efremova O I, Sidorenko L I 2000 The influence of ecdysterone on the biosynthesis of proteins and nucleic acids in mouse organs. *Khim.-Farm. Zh.* 34 3-5.

Klinzing Nielsen B K, Elgaard T, Jacobsen S E 2005 Feed additive derived from plant material originating from quinoa (*Chenopodium quinoa*). Patent application GB 2420066A.

Kuzmenko A I, Niki E, Noguchi N 2001 New functions of 20-hydroxyecdysone in lipid peroxidation. *J. Oleo. Sci.* 50, 497-506.

Lafont R, Dinan L 2003 Practical uses for ecdysteroids in mammals including humans: an update. *J. Insect Sci.* 3, pp. 30 (www.insectscience.org/3.7).

McWorther L S 2001 Biological complementary therapies: a focus on botanical products in diabetes. *Diabetes Spectrum* 14, 199-208.

Mironova V N, Kholodova, YuD, Skatchkova T F, Bonda O P, Datsenko Z M, Govseeva N N 1982 Hypocholesterolemic effects of phytoecdysones in rat experimental hypercholesterolemia. *Vopr. Med. Khim.* 28, 101-105.

Muir A D, Paton D, Ballantyne K, Aubin A A 2002 Process for recovery and purification of saponins and sapogenins from quinoa (*Chenopodium quinoa*). U.S. Pat. No. 6,355,249.

Otaka T, Uchiyama M, Okui S, Takemoto T, Hikino H, Ogawa S, Nishimoto N 1968 Stimulatory effect of insect metamorphosing steroids from Achyranthes and Cyathula on protein synthesis in mouse liver. *Chem. Pharm. Bull.* 16 2426-2429.

Pittle M H, Schmidt K, Ernst E 2005 Adverse events of herbal food supplements for body weight reduction: systematic review. *Obesity Rev.* 6, 93-111.

Purser D B, Baker S K. 1994. Ecdysones used to improve productivity of ruminants. PCT Int. Appl. WO 94 18,984, AU Appl. 93/7,397 (Chem. Abstr. 121 254587).

Rexrode K, Carey V, Hennekens C H, Walters E E, Colditz G A, Stampfer M J, Willett W C, Manson J E 1998 Abdominal adiposity and coronary heart disease in women. *JAMA* 280, 1843-1848.

Saper R B, Eisenberg D M, Phillips R S 2004 Common dietary supplements for weight loss. *Amer. Fam. Physician* 70, 1731-1738.

Simon P, Koolman J 1989 Ecdysteroids in vertebrates: pharmacological aspects. In: Koolman J (ed), Ecdysone, from chemistry to mode of action. Georg Thieme Verlag, Stuttgart, pp 254-259.

Syrov V N 2000 Comparative experimental investigations of the anabolic activity of ecdysteroids and steranabols. *Pharm. Chem. J.* 34 193-197.

Syrov, V N, Khushbaktova Z A, Abzalova MKh, Sultanov M B 1983 On the hypolipidemic and antiatherosclerotic action of phytoecdysteroids. *Dokl. Akad. Nauk Uzb. SSR* (9) 44-45.

Syrov V N, Nabiev A N, Sultanov M B 1986 The effect of phytoecdysteroids on the bile secretion function of the liver in normal rats and in animals with experimental hepatitis. *Farmakol. Toksikol.* 49 100-103.

Takahashi H, Nishimoto K 1992 Antidiabetic agents containing ecdysterone or inokosterone. Jpn Kokai Tokkyo Koho J. P. 04,125,135 [92 124,135]. (Chem. Abstr. 117: 84874b).

Uchiyama M, Ogawa S. 1970. Hypoglycemic formulations containing insect hormones. Application JP 19690506 (Chem. Abstr. 74: 24985).

Unger R H 2003 Minireview: weapons of lean body mass destruction: the role of ectopic lipids in the metabolic syndrome. *Endocrinology* 144, 5159-5165.

Wasan K M, Looije N A 2005 Emerging pharmacological approaches in the treatment of obesity. *J. Pharm. Pharmaceut. Sci.* 8, 259-271.

Yang C, Zhang G, Liu X, Wang C 2001 Oral antidiabetic compositions containing—ecdysone from *Cyanothis arachnoides*. Appl. CN-2000-10637/20000612 (Chem. Abstr. 135: 127188).

Zhu N, Kikusaki H, Vastano B C, Nakatani N, Karwe M V, Rosen R T, Ho C T 2001 Ecdysteroids of quinoa seeds (*Chenopodium quinoa* Willd.). *J. Agric. Food Chem.* 49, 2576-2578.

The invention claimed is:

1. A method for diminishing the abdominal fat mass in overweight or obese humans, comprising administering to a human in need thereof, administering a 20-hydroxyecdysone-based composition, wherein the 20-hydroxyecdysone is administered in a dose comprised between 0.3 and 0.5 mg/kg per day, said 20-hydroxyecdysone being supplied as pure 20-hydroxyecdysone or in a saponin-free quinoa extract.

2. The method for diminishing the abdominal fat mass in overweight or obese humans according to claim 1, wherein human in need thereof has a weight excess or is obese, the human in need thereof suffers from metabolic syndrome, and the metabolic syndrome is treated by diminishing the abdominal fat mass.

3. The method according to claim 1, wherein the 20-hydroxyecdysone is supplied in the form of a saponin-free quinoa extract comprising between 1% and 7% in weight of the 20-hydroxyecdysone.

4. The method according to claim 3, wherein the saponin-free quinoa extract comprises 2% in weight of 20-hydroxyecdysone.

5. The method according to claim 1, wherein the composition is administered in the form of a food or a dietary supplement.

6. The method according to claim 1, wherein the composition is administered in the form of a medicinal composition.

* * * * *